US006630348B1

(12) United States Patent
Lee et al.

(10) Patent No.: US 6,630,348 B1
(45) Date of Patent: Oct. 7, 2003

(54) SINGLE-CHAIN INSULIN ANALOG AND A POLYNUCLEOTIDE SEQUENCE ENCODING THE ANALOG

(76) Inventors: Hyun Chul Lee, Seodaemungu Hongeundong 268, Dongdo-academyhouse A-402, Seoul (KR); Su-Jin Kim, Dukyanggu Haengsindong 938 Haibit 1819-1304, Goyangsi (KR); Kyung Sup Kim, Yongdeungpogu Yeoyeedodong Samik, Apt. B-202, Seoul (KR); Hang-Cheol Shin, Seochogu Wonjidong 401-37, Seoul (KR); Ji-Won Yoon, 206 Edgeview Drive, N.W., Calgary, Alberta (CA), T3A 4X5

( * ) Notice: Subject to any disclaimer, the term of this patent is extended or adjusted under 35 U.S.C. 154(b) by 0 days.

(21) Appl. No.: 09/706,690

(22) Filed: Nov. 7, 2000

(30) Foreign Application Priority Data

Oct. 2, 2000 (KR) ........................................ 2000-58003

(51) Int. Cl.⁷ ........................ A61K 38/28; C07H 21/04; C12N 5/00; C12N 7/00; C12N 15/00
(52) U.S. Cl. .................. 435/325; 424/192.1; 435/69.7; 435/235.1; 435/320.1; 435/254.11; 435/252.3; 530/303; 536/23.5; 514/3
(58) Field of Search ................................ 530/300, 303, 530/350; 424/184.1, 192.1, 198.1; 514/2, 44, 3, 12; 536/23.1, 23.5; 435/69.7, 235.1, 325, 252.3, 320.1, 254.11

(56) References Cited

U.S. PATENT DOCUMENTS 5,962,267 A * 10/1999 Shin et al. .................. 435/69.4

FOREIGN PATENT DOCUMENTS

| EP | 0741188 A2 | * 11/1996 |
| GB | 2298206 A | * 2/1996 |

OTHER PUBLICATIONS

Lee et al. Remission in models of type 1 diabetes by gene therapy using a single–chain insulin analogue. Nature 408: 483–488, 2000.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res. 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure predicition, and the Levinthal paradox. The Protein Folding Problem and Tertiary Structure Prediction, pp. 492–495, 1994.*
Brems et al. Altering the association properties of insulin by amino acid replacement. Protein Engineering 5(6): 527–533, 1992.*
Schwartz et al. A superactive insulin [B10–Aspartic acid] insulin(human). Proc Natl Acad Sci USA 84: 6408–6411, 1987.*
Brange et al. Monometric insulins obtained by protein engineering and their medical implications. Nature 333(16): 679–682, 1988.*
Goeddel et al. Expression in *Escherichia coli* of chemically synthesized genes for human insulin. Proc Natl Acad Sci USA 76(1): 106–110, 1979.*
Thim et al. Secretion and processing of insulin precursors in yeast. Proc Natl Acad Sci USA 83: 6766–6770, 1986.*
Markussen et al. Soluble, prolonged–acting insulin derivatives.III. Degree of protraction, crystallizability and chemical stability of insulins substituted in positions A21, B13, B23, B27, and B30. Protein Engineering 2(2): 157–166, 1988.*
Gokhale et al. Role of linkers in communication between protein modules. Curr Opin Chem Biol 4: 22–27, 2000.*

* cited by examiner

*Primary Examiner*—Elizabeth Kemmerer
*Assistant Examiner*—Bridget E. Bunner
(74) *Attorney, Agent, or Firm*—Birch, Stewart, Kolasch & Birch, LLP

(57) ABSTRACT

The subject matter of the invention is directed to a single-chain insulin analog that is used to treat diabetes by gene therapy methods.

11 Claims, 7 Drawing Sheets

(1 of 7 Drawing Sheet(s) Filed in Color)

SEQUENCE LISTING

```
<160> NUMBER OF SEQ ID NOS: 18

<210> SEQ ID NO 1
<211> LENGTH: 7
<212> TYPE: PRT
<213> ORGANISM: synthetic construct

<400> SEQUENCE: 1

Gly Gly Gly Pro Gly Lys Arg
1               5

<210> SEQ ID NO 2
<211> LENGTH: 7
<212> TYPE: PRT
<213> ORGANISM: synthetic construct

<400> SEQUENCE: 2

Arg Arg Gly Pro Gly Gly Gly
1               5
```

```
<210> SEQ ID NO 3
<211> LENGTH: 183
<212> TYPE: DNA
<213> ORGANISM: synthetic construct

<400> SEQUENCE: 3
atgttcgtta atcagcacct gtgcggctct cacctggtag aagctctgta cctggtttgc      60
ggtgaacgtg gttttttcta cccccgaaa accggtggtg gtccgggtaa acgtggcatc     120
gttgaacaat gctgtactag catctgctct ctctaccagc tggagaacta ttgtaactag     180
taa                                                                   183

<210> SEQ ID NO 4
<211> LENGTH: 7
<212> TYPE: PRT
<213> ORGANISM: synthetic construct

<400> SEQUENCE: 4

Gly Gly Gly Gly Gly Lys Arg
1               5

<210> SEQ ID NO 5
<211> LENGTH: 7
<212> TYPE: PRT
<213> ORGANISM: synthetic construct

<400> SEQUENCE: 5

Arg Arg Gly Gly Gly Gly Gly
1               5

<210> SEQ ID NO 6
<211> LENGTH: 9
<212> TYPE: PRT
<213> ORGANISM: synthetic construct

<400> SEQUENCE: 6

Gly Gly Ala Pro Gly Asp Val Lys Arg
1               5

<210> SEQ ID NO 7
<211> LENGTH: 9
<212> TYPE: PRT
<213> ORGANISM: synthetic construct

<400> SEQUENCE: 7

Arg Arg Ala Pro Gly Asp Val Gly Gly
1               5

<210> SEQ ID NO 8
<211> LENGTH: 9
<212> TYPE: PRT
<213> ORGANISM: synthetic construct

<400> SEQUENCE: 8

Gly Gly Tyr Pro Gly Asp Val Lys Arg
1               5

<210> SEQ ID NO 9
<211> LENGTH: 9
<212> TYPE: PRT
<213> ORGANISM: synthetic construct

<400> SEQUENCE: 9

Arg Arg Tyr Pro Gly Asp Val Gly Gly
```

-continued

```
<210> SEQ ID NO 10
<211> LENGTH: 9
<212> TYPE: PRT
<213> ORGANISM: synthetic construct

<400> SEQUENCE: 10

Gly Gly His Pro Gly Asp Val Lys Arg
1               5

<210> SEQ ID NO 11
<211> LENGTH: 9
<212> TYPE: PRT
<213> ORGANISM: synthetic construct

<400> SEQUENCE: 11

Arg Arg His Pro Gly Asp Val Gly Gly
1               5

<210> SEQ ID NO 12
<211> LENGTH: 63
<212> TYPE: DNA
<213> ORGANISM: synthetic construct

<400> SEQUENCE: 12
ttagctcggc ttattccagg ggtgtgtttc gtcgagattt cgttaatcag cacctgtgcg      60
gct                                                                   63

<210> SEQ ID NO 13
<211> LENGTH: 63
<212> TYPE: DNA
<213> ORGANISM: synthetic construct

<400> SEQUENCE: 13
agagaaaaag aagggaaata aaggttaccc acttcatgga tccgcccagt cgtcgacgct      60
gct                                                                   63

<210> SEQ ID NO 14
<211> LENGTH: 22
<212> TYPE: DNA
<213> ORGANISM: synthetic construct

<400> SEQUENCE: 14
gtaatacgac tcactatagg gc                                              22

<210> SEQ ID NO 15
<211> LENGTH: 26
<212> TYPE: DNA
<213> ORGANISM: synthetic construct

<400> SEQUENCE: 15
atttcgaata agaagaggaa gggaag                                          26

<210> SEQ ID NO 16
<211> LENGTH: 28
<212> TYPE: DNA
<213> ORGANISM: synthetic construct

<400> SEQUENCE: 16
gcgcaagctt ttactagtta caatagtt                                        28
```

```
<210> SEQ ID NO 17
<211> LENGTH: 28
<212> TYPE: DNA
<213> ORGANISM: synthetic construct

<400> SEQUENCE: 17
gcgcggatcc atgttcgtta atcagcac                                              28

<210> SEQ ID NO 18
<211> LENGTH: 28
<212> TYPE: DNA
<213> ORGANISM: synthetic construct

<400> SEQUENCE: 18
gcgcaagctt ttactagtta caatagtt                                              28
```

SINGLE-CHAIN INSULIN ANALOG AND A POLYNUCLEOTIDE SEQUENCE ENCODING THE ANALOG

BACKGROUND OF THE INVENTION

The present invention relates to a method of introducing at least one single-chain insulin analog protein or a gene encoding a single-chain insulin analog (SIA) into at least one mammalian tissue for use in treating diabetes in the mammalian host. The present invention also relates to the single-chain insulin analog and a recombinant vector construct comprising the gene encoding SIA.

The cure of diabetes has long been sought using several different approaches, including islet transplantation, regeneration of β cells and insulin gene therapy (Levine, F. & Leibowitz, G. Towards gene therapy of diabetes mellitus. *Mol. Med. Today* 5, 165–171 (1999)). However, the permanent remission of type 1 diabetes has not yet been satisfactorily achieved.

WO96/34882 discusses making single chain insulin with high bioactivity, but does not disclose the single chain insulin analog of the invention.

There remains a very real and substantial need for a method of introducing at least one gene encoding a single-chain insulin analog to at least one cell of a mammalian host in vitro or in vivo, for use in treating the mammalian host suffering from diabetes.

SUMMARY OF THE INVENTION

The present invention has met the hereinbefore described need.

A method of introducing at least one gene encoding a product into at least one cell of a mammalian tissue for use in treating a mammalian host is provided in the present invention. This method includes employing recombinant techniques to produce a DNA vector molecule containing the gene coding for the product and introducing the DNA vector molecule containing the gene coding for the product into the tissue cell. The DNA vector molecule can be any DNA molecule capable of being delivered and maintained within the target cell or tissue such that the gene encoding the product of interest can be stably expressed. The DNA vector molecule preferably utilized in the present invention is either a viral or plasmid DNA vector molecule. This method preferably includes introducing the gene encoding the product into the cell of the mammalian tissue for a therapeutic use.

An object of the invention is to provide a single-chain insulin analog compound of formula (I) having the properties of greater insulin receptor binding activity than proinsulin and less insulin receptor binding activity than insulin:

$$\text{B chain-X-A chain} \qquad (I)$$

wherein:

B and A chains are the human insulin chains, respectively, or functional analogs thereof; and X is a joining peptide of from 5 to 18 amino acids.

In the above compound, preferably, X may be from 6 to 9 amino acids.

Also, in the above compound, when X has the formula $U_l$—$Z_n$—$Y_m$—$Z_l$—$U_n$, the following limitations may be placed:

U is an arginine or lysine residue;

Z is an amino acid residue;

Y is a peptide;

l is an integer of 2–n;

n is an integer of 0, 1 or 2; and m is an integer of 2 to 5

In this compound, Z may be glycine; and Y may be glycine-proline-glycine. Furthermore, Z may be glycine; and Y may be alanine-proline-glycine-aspartic acid-valine. Alternatively, Z may be glycine; and Y may be tyrosine-proline-glycine-aspartic acid-valine. Further, Z may be glycine; and Y may be histidine-proline-glycine-aspartic acid-valine.

Another object of the invention is to provide a polynucleotide encoding the single-chain insulin analog described above. Another embodiment of the invention includes a recombinant vector comprising the polynucleotide that encodes the single chain insulin analog described above. The vector may be a plasmid or a virus. If a virus, preferably, it is adeno-associated virus. Moreover, it is preferred that the promoter be inducible. More preferably, the promoter may be regulated by glucose. Even more preferably, the promoter is a pyruvate kinase gene promoter. Most preferably, the promoter is the hepatocyte-specific L-type pyruvate kinase gene promoter.

The invention is also directed to a cell line transformed with the above-described vector.

Another embodiment of the invention is directed to a method for treating a patient suffering from diabetes comprising:

a) generating a recombinant viral or plasmid vector comprising a polynucleotide encoding a single-chain insulin analog operatively linked to a promoter; and b) introducing said recombinant viral or plasmid vector to said patient, such that expression of said polynucleotide within said patient results in remission of diabetes.

Preferably, the viral vector is adeno-associated virus, and the promoter is an inducible promoter. Preferably, the promoter is regulated by glucose. In the method described above, preferably the dosage of said viral vector is at least about $10^{11}$ viral particles. Preferably, the treatment method is accomplished by using a vector that is introduced to the patient through the cell line comprising the single chain insulin analog described above.

The present invention is also directed to a method for treating a patient suffering from diabetes comprising administering the single chain insulin analog compound described above to a patient in need thereof. Preferably, the diabetes is type I diabetes.

These and other objects of the invention will be more fully understood from the following description of the invention, the referenced drawings attached hereto and the claims appended hereto.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 1A:
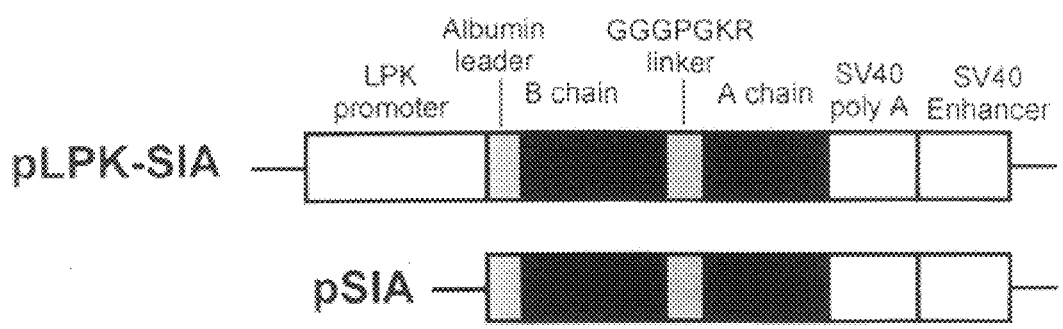
FIGS. 1A–1C.—Construction of pLPK-SIA, hypoglycemic effect of pLPK-SIA and hepatocyte-specific expression of pLPK-SIA.

1A. Diagram of pLPK-SIA construct showing LPK promoter, albumin leader sequence, SIA cDNA, SV40 poly (A) sequence and SV40 enhancer and diagram of pSIA.

1B. Transient hypoglycemic effect of pLPK-SIA. When blood glucose levels in STZ-induced diabetic rats were over 500 mg/dl, 30 μg of pSIA or pLPK-SIA was mixed with 60 μl of FuGENE™ (a 6 cationic multimeric fusion gene from Boehringer Mannheim, Mannheim, Germany) and injected into the hepatic portal vein, and blood glucose levels were measured. Each time point represents the mean±SD value.

1C. SIA DNA is detected in both pSIA- and pLPK-SIA-treated rats, but SIA is expressed only in pLPK-SIA-treated rats. DNA or total RNA for PCR or RT-PCR was isolated from the liver (Li), kidney (K), spleen (S), lung (L) and heart (H) of rats 5 days after treatment with pSIA or pLPK-SIA.

FIGS. 2A–2J.—Hypoglycemic effect of rAAV-LPK-SIA, integration of rAAV-LPK-SIA into chromosomal DNA in hepatocytes and expression of SIA.

2A. Different doses of rAAV-LPK-SIA ($1\times10^9$–$10^{12}$ particles) were injected into the hepatic portal vein of STZ-induced diabetic SD rats (11–13weeks old, >500 mg/dl blood glucose; n=10/group), and blood glucose levels were measured up to 38 weeks after rAAV-LPK-SIA treatment. Each time point represents the mean±SD value. The mean blood glucose levels of normal control SD rats (n=10) was 103±10 mg/dl. All animals treated with $10^9$ particles died at 25 weeks after treatment, whereas 30% of the animals treated with $10^{10}$ particles remained alive at 38 weeks after treatment.

2B. The restriction enzyme map of LPK-SIA and the region that was used as a probe are shown. Total cellular DNA was isolated from the livers of STZ-induced diabetic SD rats at 5 days, 5 weeks, 15 weeks and 25 weeks after administration of $1\times10^{11}$ virus particles of rAAV-LPK-SIA. After digestion of chromosomal DNA with XbaI, Southern blot hybridization was performed using a $^{32}$P-labelled probe containing the SIA, SV40 poly(A) and SV40 enhancer sequences. The XbaI-digested psub201-LPK-SIA (10 pg, 100 pg) and chromosomal DNA from normal control SD rats (NC) were used as a positive and negative control, respectively.

The digestion of DNA from hepatocytes at 25 weeks after rAAV-LPK-SIA treatment with non-cutting enzymes that have no restriction sites in the rAAV-LPK-SIA genome showed differently sized, single molecular weight bands that were much larger than the 4.3 Kb band (arrow), suggesting that rAAV-LPK-SIA DNA is integrated into chromosomal DNA (center panel). The digestion with single cutting enzymes showed a 4.3 Kb band (arrow) and one differently sized band, suggesting that the rAAV-LPK-SIA DNA is integrated into the chromosomal DNA in a head-to-tail concatemeric manner (right panel).

Immunocytochemical staining of SIA in the liver of 2C. rAAV-LPK-SIA-treated, at 1 month after treatment and 2D. normal control rats. SIA is expressed in the hepatocytes of only the rAAV-LPK-SIA-treated rats.

Histological examination of liver tissue from 2E. rAAV-LPK-SIA-treated, at 1 month after treatment and 2F. normal control rats by hematoxylin and eosin staining.

Immunohistochemical staining of insulin in the pancreatic islet of 2G. rAAV-LPK-SIA-treated rats, at 1 month after treatment and 2H. normal control rats.

2I. Plasma SIA levels were measured at 0 (gray bars) and 4 (black bars) hrs after glucose loading (2 g/kg body weight) at 5, 10, 15, 20 and 25 weeks after rAAV-LPK-SIA treatment (n=7/group).

2J. Plasma C-peptide levels were measured at 0 (gray bars) and 0.5 (black bars) hr after glucose loading at 25 weeks after rAAV-LPK-SIA treatment (n=7). Normal non-diabetic rats (NC; n=7) and untreated STZ-induced diabetic rats(STZ rat; n=7) were used as controls. Values are means±SD.

FIGS. 3A–3G.—The functional response of SIA to glucose in rAAV-LPK-SIA-treated STZ-induced diabetic rats. rAAV-LPK-SIA ($1\times10^{11}$ particles) was injected into the hepatic portal vein of STZ-induced diabetic SD rats. At 30 weeks after the treatment, different levels of blood glucose (about 100 (saline-treated), 300 or 500 mg/dl) were maintained for 30 min using a hyperglycemic clamp.

3A. The presence of SIA DNA,

3B. The expression of SIA in the hepatocytes and

3C. The production of SIA in the plasma was determined at 0 (gray bars) and 4 (black bars) hrs (n=7/group). At 4 weeks after treatment, rats (15–17 weeks old) were fasted for 4 hrs and a GTT was performed. Blood samples were collected from the tail vein at the indicated times following the injection of glucose, and levels of:

3D. glucose and 3E. insulin or SIA were measured. (NC), normal control rats; (rAAV-LPK-SIA), rAAV-LPK-SIA-treated rats ($1\times10^{11}$ particles). Each time point represents the mean±SD value.

3F. Western blot analysis of SIA. The release of SIA was examined in plasma collected at 0, 2, 4 and 6 hrs after glucose loading by western blot using anti-SIA antibodies. As a control, the recombinant SIA protein was used. NR, non-reducing conditions; R, reducing conditions.

3G. The expression of SIA mRNA was examined in the liver at 0, 2, 4 and 6 hrs after glucose loading by RNase protection assay.

FIGS. 4A–4E.—Remission of autoimmune diabetes in NOD mice by administration of rAAV-LPK-SIA.

4A. Diabetic NOD mice were administered $1\times10^{12}$virus particles of rAAV-SIA or rAAV-LPK-SIA per mouse (n=6/group), and blood glucose was measured.

4B. shows the integration of SIA DNA into the hepatocyte chromosomal DNA. Total cellular DNA was isolated from the livers of NOD mice at 15 weeks after rAAV-LPK-SIA treatment and digested with the indicated restriction enzymes. Southern blot hybridization was performed. The band pattern was the same as that in rAAV-LPK-SIA-treated rats, indicating that rAAV-LPK-SIA DNA is integrated into the chromosomal DNA (arrows, 4.3 Kb band).

4C. The expression of SIA mRNA in hepatocytes (NC, untreated control NOD mice) and 4D. the production of SIA in the plasma was measured at 0 (gray bars) and 4 (black bars) hrs after glucose loading (2 g/kb body weight) at 5, 10 or 15 weeks after rAAV-LPK-SIA treatment (n=5/group).

4E. GTT test was performed in rAAV-LPK-SIA-treated diabetic NOD mice (n=5) after the remission of diabetes and in age-matched normal control NOR mice (NC, n=7). Each time point represents the mean±SD value.

DETAILED DESCRIPTION OF THE INVENTION

As used herein, the term "patient" includes members of the animal kingdom including but not limited to human beings.

As used herein, the term "mammalian host" includes members of the animal kingdom including but not limited to human beings.

As used herein, the term "diabetes" is a hormonal disorder. Insulin is needed to control the blood sugar levels.

As used herein, the term "Type I diabetes" means insulin-dependent diabetes mellitus (IDDM).

As used herein, the term "Type II diabetes" means non insulin-dependent diabetes mellitus (NIDDM).

Insulin is composed of two peptide chains referred to as the A chain and B chain. A and B chains are linked together by two disulfide bonds, and an additional disulfide is formed within the A chain. In most species, the A chain consists of 21 amino acids and the B chain of 30 amino acids. Although the amino acid sequence of insulin varies among species, certain segments of the molecule are highly conserved, including the positions of the three disulfide bonds, both ends of the A chain and the C-terminal residues of the B chain. These similarities in the amino acid sequence of insulin lead to a three dimensional conformation of insulin that is very similar among species, and insulin from one animal is very likely biologically active in other species. Indeed, pig insulin has been widely used to treat human patients.

Insulin molecules have a tendency to form dimers in solution due to hydrogen-bonding between the C-termini of B chains. Additionally, in the presence of zinc ions, insulin dimers associate into hexamers.

These interactions have important clinical ramifications. Monomers and dimers readily diffuse into blood, whereas hexamers diffuse very poorly. Hence, absorption of insulin preparations containing a high proportion of hexamers is delayed and slow. This problem, among others, has stimulated development of a number of recombinant insulin analogs. The first of these molecules to be marketed—called insulin lispro—is engineered such that lysine and proline residues on the C-terminal end of the B chain are reversed; this modification does not alter receptor binding, but minimizes the tendency to form dimers and hexamers.

As used herein, the "single-chain insulin analog (SIA)" encompasses a group of structurally-related proteins wherein the A and B chains are covalently linked by a polypeptide linker. SIA has the properties of greater insulin receptor binding activity and/or glucose uptake activity than proinsulin, and less insulin receptor binding activity and glucose uptake activity than insulin. "SIA-1", "SIA-2" and so on belong to the SIA group.

The polypeptide linker connects the C-terminus of the B chain to the N-terminus of the A chain. The linker may be of any length so long as the linker provides the structural conformation necessary for SIA to have a glucose uptake and insulin receptor binding effect. Preferably, the linker is about 5–18 amino acids long. Preferably, it is 6–12 amino acids long. Even more preferably, it is 6–9 amino acids long. Most preferably it is 7 amino acids long. The most preferred sequence for the linker are Gly-Gly-Gly-Pro-Gly-Lys-Arg (SEQ ID NO:1) or Arg-Arg-Gly-Pro-Gly-Gly-Gly (SEQ ID NO:2). However, it should be understood that many variations of this sequence are possible such as in the length (both addition and deletion) and substitutions of amino acids without substantially compromising the effectiveness of the produced SIA in glucose uptake and insulin receptor binding activities. For example, several different amino acid residues may be added or taken off at either end without substantially decreasing the activity of the produced SIA. In addition, the amino acid Gly may be replaced with any amino acid residue.

It is also to be understood that the insulin A and B chains may be modified or fragmented so long as the modified or fragmented form has glucose uptake activity and/or binds to the insulin receptor, wherein a SIA formed from these chains possesses greater insulin receptor binding activity and/or glucose uptake activity than proinsulin, and less insulin receptor binding activity and glucose uptake activity than insulin.

As used herein, a "promoter" can be any sequence of DNA that is active, and controls transcription in an eucaryotic cell. Preferably, the promoter is active in mammalian cells. The promoter may be constitutively expressed or inducible. Preferably, the promoter is inducible. Preferably, the promoter is inducible by an external stimulus. More preferably, the promoter is inducible by hormones or metabolites. Still more preferably, the promoter is regulatable by glucose. Even more preferably, the promoter is a pyruvate kinase gene promoter. Most preferably, the promoter is a hepatocyte-specific L-type pyruvate kinase gene promoter.

Likewise, "enhancer elements", which also control transcription, can be inserted into the DNA vector construct, and used with the construct of the present invention to enhance the expression of the gene of interest.

As used herein viral vectors include any virus that is useful in in vivo or ex vivo gene therapy protocols. Preferably, the virus is non-pathogenic. More preferably, the virus is adeno-associated virus (AAV).

As used herein, the term "DC-chol" means a cationic liposome containing cationic cholesterol derivative. The "DC-chol" molecule includes a tertiary amino group, a medium length spacer arm (two atoms) and a carbamoyl linker bond (Gao et al., Biochem. Biophys. Res, Commun., 179:280–285, 1991).

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

The present invention discloses in vivo techniques for delivery of a DNA sequence of interest to the tissue cells of the mammalian host. The in vivo technique involves directly administering a DNA vector containing a DNA sequence of interest or other delivery vehicle of interest into the tissue cells, to the target area of the mammalian host, so as to effect in vivo expression of the gene product of interest. The vector is preferably a viral vector.

Alternatively, the present invention discloses ex vivo and in vivo techniques for delivery of a DNA sequence of interest to the tissue cells of the mammalian host. The ex vivo technique involves culturing target tissue cells, in vitro transfecting a DNA vector containing a DNA sequence of interest or other delivery vehicle of interest into the tissue cells, followed by transplantation of the modified tissue cells to the target area of the mammalian host, so as to effect in vivo expression of the gene product of interest.

As an alternative to the in vitro manipulation of cells, the gene encoding the product of interest is introduced into liposomes and injected directly into the target area, where the liposomes fuse with the tissue cells, resulting in an in vivo gene expression of SIA.

As an additional alternative to the in vitro manipulation of tissue cells, the gene encoding the product of interest is introduced into the target area as naked DNA. The naked DNA enters the tissue cell, resulting in an in vivo gene expression of SIA.

One ex vivo method of treating diabetes comprises initially generating a recombinant viral or plasmid vector which contains a DNA sequence encoding single-chain insulin analog or biologically active fragment thereof. This recombinant vector is then used to infect or transfect a population of in vitro cultured tissue cells, resulting in a population of cells containing the vector. Expression of this DNA sequence of interest is useful in substantially reducing at least one deleterious pathology associated with diabetes.

More specifically, this method includes employing SIA, or a biologically active derivative or fragment thereof or a biologically active derivative or fragment thereof.

A further embodiment of the present invention includes employing SIA or a biologically active derivative or fragment thereof, and employing as the DNA plasmid vector any DNA plasmid vector known to one of ordinary skill in the art capable of stable maintenance within the targeted cell or tissue upon delivery, regardless of the method of delivery utilized.

One such method is the direct delivery of the DNA vector molecule, whether it be a viral or plasmid DNA vector molecule, to the target cell or tissue. This method also includes employing SIA or biologically active derivative or fragment thereof.

Another embodiment of this invention provides a method for introducing at least one gene encoding a product into at least one cell of a target tissue for use in treating the mammalian host. This method includes employing non-viral means for introducing the gene coding for the product into the tissue cell. More specifically, this method includes a liposome encapsulation, calcium phosphate coprecipitation, electroporation, or DEAE-dextran mediation, and includes employing as the gene a gene capable of encoding a member of transforming growth factor superfamily or biologically active derivative or fragment thereof, or biologically active derivative or fragment thereof.

Another embodiment of this invention provides an additional method for introducing at least one gene encoding a product into at least one cell of a tissue for use in treating the mammalian host. This additional method includes employing the biologic means of utilizing a virus to deliver the DNA vector molecule to the target cell or tissue. Preferably, the virus is a pseudo-virus, the genome having been altered such that the pseudo-virus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. Preferably, the viral vector is adeno-associated virus.

A preferred method of the present invention involves direct in vivo delivery of a SIA gene to the target tissue of a mammalian host through use of an adeno-associated virus (AAV) vector. In other words, a DNA sequence of interest encoding a functional SIA protein or SIA fragment is subcloned into the respective viral vector. The SIA containing viral vector is then grown to adequate titer and directed into the targeted area, preferably by injection into the portal vein.

Direct injection of a DNA molecule containing the gene of interest into the joint results in transfection of the recipient tissue cells and hence bypasses the requirement of removal, in vitro culturing, transfection, selection, as well as transplanting the DNA vector containing-cell to promote stable expression of the heterologous gene of interest.

Methods of presenting the DNA molecule to the target tissue includes, but is not limited to, encapsulation of the DNA molecule into cationic liposomes, subcloning the DNA sequence of interest in a retroviral or plasmid vector, or the direct injection of the DNA molecule itself into the targeted area. The DNA molecule is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the targeted tissue.

In a preferred embodiment, tissue cells recovered from the patient are cultured in vitro for subsequent utilization as a delivery system for gene therapy. It will be apparent that Applicants are not limited to the use of the specific tissue type or source disclosed. It would be possible to utilize other tissue sources for in vitro culture techniques. The method of using the gene of this invention may be employed both prophylactically and in the therapeutic treatment of diabetes.

In another embodiment of this invention, a compound for parenteral administration to a patient in a therapeutically effective amount is provided that contains a gene encoding a SIA protein and a suitable pharmaceutical carrier.

Another embodiment of this invention provides for a compound for parenteral administration to a patient in a prophylactically effective amount that includes a gene encoding a SIA protein and a suitable pharmaceutical carrier.

A further embodiment of this invention includes the method as hereinbefore described including introducing the gene into the cell in vitro. This method also includes subsequently transplanting the infected cell into the mammalian host. This method includes after effecting the transfecting of the tissue cell but before the transplanting of the infected cell into the mammalian host, storing the transfected tissue cell. It will be appreciated by those skilled in the art that the infected tissue cell may be stored frozen in 10 percent DMSO in liquid nitrogen. This method includes employing a method to substantially prevent the development of diabetes in a mammalian host having a high susceptibility of developing diabetes.

Another embodiment of this invention includes a method of introducing at least one gene encoding a product into at least one cell of a target tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by injection through the portal vein. This method includes employing the method to substantially prevent the development of diabetes in a mammalian host having a high susceptibility of developing diabetes. This method also includes employing the method on a diabetic mammalian host for therapeutic use.

In a preferred embodiment, the inventors generated a single chain insulin analog (SIA), which possesses biologically active insulin activity without processing and produced a recombinant adeno-associated virus expressing SIA (rAAV-LPK-SIA) under the control of hepatocyte-specific L-type pyruvate kinase gene promoter which regulates SIA expression depending on the level of blood glucose. When the inventors administered rAAV-LPK-SIA through the portal vein of streptozotocin (STZ)-induced diabetic rats, the blood glucose levels decreased, reaching the level of normoglycemia in 1 week and maintained a normoglycemic state for more than 6 months without hypoglycemia or any apparent side effects. In addition, the treatment of diabetic NOD mice with rAAV-LPK-SIA resulted in the complete remission of autoimmune diabetes as seen in STZ-induced diabetes. This novel SIA gene therapy is believed to have therapeutic value for the cure of autoimmune diabetes in humans.

The following examples are offered by way of illustration of the present invention, and not by way of limitation.

EXAMPLES

Example 1

Materials and Methods

Cloning and Expression of Single Chain Insulin Analog (SIA) DNA in *E. coli*

SIA-1 DNA encoding Gly-Gly-Gly-Pro-Gly-Lys-Arg sequence in the linker region of SIA was generated by polymerase chain reaction (PCR) using five overlapping oligonucleotides of 65–68 bases in length. The SIA-1 DNA was constructed by considering the codon usage of *E. coli* to increase the expression level of SIA in the bacterial hosts. The resulting SIA-1 DNA sequence was: ATG/TTC/GTT/AAT/CAG/CAC/CTG/TGC/GGC/TCT/CAC/CTG/GTA/GAA/GCT/CTG/TAC/CTG/GTT/TGC/GGT/GAA/CGT/GGT/TTT/TTC/TAC/ACC/CCG/AAA/ACC/GGT/GGT/GGT/CCG/GGT/AAA/CGT/GGC/ATC/GTT/GAA/CAA/TGC/TGT/ACT/AGC/ATC/TGC/TCT/CTC/TAC/CAG/CTG/GAG/AAC/TAT/TGT/AAC/TAG/TAA (SEQ ID NO:3). The N-terminal pentapeptide sequence (PSDKP) of TNF-α was used as a fusion partner to produce SIA-1 with high-level expression in *E. coli*. For convenience in the purification process, 10 histidine residues and a methionine residue for chemical cleavage were inserted between the PSDKP sequence and SIA-1. A DNA fragment encoding the PSDKP sequence and 10 histidine residues was chemically synthesized. After digestion with restriction endonucleases NdeI and BamHI, the DNA fragment was inserted downstream of the T7 promoter of the expression plasmid pET-3a, which was linearized with the same restriction endonucleases, and the resulting plasmid was named pET. The gene encoding SIA-1 was digested with BamHI and HindIII and inserted into the BamHI and HindIII enzyme restriction sites of the pET plasmid and the resulting plasmid was named pET-SIA-1. This expression plasmid was then used to transform *E. coli* BL21 (DE3) cells, and the fused single chain insulin analog was expressed as inclusion bodies. The inclusion bodies of the fusion protein were sulfonated at their cysteine residues and chemically cleaved by CNBr treatment. S-sulfonated SIA-1 was purified by cation-exchange chromatography (Pharmacia Biotechnology) and refolded by addition of β-mercaptoethanol and analyzed by analytical reverse-phase HPLC. Briefly, sulfonated SIA-1 (0.37 mg/ml) was converted to SIA-1 with native disulfide pairings in 50 mM glycine buffer, pH 11.0, at 4° C. using 2 equivalents of β-mercaptoethanol. After 20 hr, the protein solution was acidified to pH 2.5 to terminate the reaction, loaded onto a Zorbax C8 column and eluted with a linear gradient of 90% acetonitrile. The fractions containing the desired material were pooled, frozen and lyophilized.

Other SIA DNAs encoding Arg-Arg-Gly-Pro-Gly-Gly-Gly, Gly-Gly-Gly-Gly-Gly-Lys-Arg (SEQ ID NO:4), Arg-Arg-Gly-Gly-Gly-Gly-Gly (SEQ ID NO:5), Gly-Gly-Ala-Pro-Gly-Asp-Val-Lys-Arg (SEQ ID NO:6), Arg-Arg-Ala-Pro-Gly-Asp-Val-Gly-Gly (SEQ ID NO:7), Gly-Gly-Tyr-Pro-Gly-Asp-Val-Lys-Arg (SEQ ID NO:8), Arg-Arg-Tyr-Pro-Gly-Asp-Val-Gly-Gly (SEQ ID NO:9), Gly-Gly-His-Pro-Gly-Asp-Val-Lys-Arg ((SEQ ID NO: 10) and Arg-Arg-His-Pro-Gly-Asp-Val-Gly-Gly (SEQ ID NO:11) sequence in the linker region of SIA, respectively, were prepared by PCR using the SIA-1 gene as a template DNA. These genes were digested with BamHI and HindIII and inserted into plasmid pET. The resulting plamids were named pET-SIA-2, pET-SIA-3, pET-SIA-4, pET-SIA-5, pET-SIA-6, pET-SIA-7, pET-SIA-8 and pET-SIA-9, respectively. These expression plasmids were then used to transform *E. coli* BL21 (DE3) cells, and the fused SIAs were expressed as inclusion bodies. The purification processes for SIAs were essentially the same as that of SIA-1.

Examination of Functional Activity of Recombinant SIA Produced in *E. coli*

Insulin receptor binding and glucose uptake assays were performed using IM-9 lymphocytes as described previously (Pollet, R. J., Standaert, M. L. & Haase, B. A. Insulin binding to the human lymphocyte receptor. Evaluation of the negative cooperativity model. *J. Biol. Chem.* 252, 5828–5834 (1977); Roth, J. Assay of peptide hormones using cell receptors: application to insulin and to human growth hormone. *Methods Enzymol.* 37, 66–82 (1975); and Frost, S. C. & Lane, M. D. Evidence for the involvement of vicinal sulfhydryl groups in insulin-activated hexose transport by 3T3-L1 adipocytes. *J. Biol. Chem.* 260, 2646–2652 (1985)). To study the in vivo hypoglycemic activity of SIA, 8–10 week-old male Sprague-Dawley rats at 200 g to 250 g in body weight, as described previously (Heath, W. F., et al. (A-C-B) human proinsulin, a novel insulin agonist and intermediate in the synthesis of biosynthetic human insulin. *J. Biol. Chem.* 267, 419–425 (1992)), were fasted, and SIA protein (4 to 80 µg in 0.1 ml saline/100 g body weight) or the same volume of saline as a control was injected subcutaneously. Blood was obtained from the tail vein of each rat and the glucose level was determined before (time zero) and 30 min, 1, 2, 3 and 4 h after administration of SIA. The mean percentage change in the blood glucose level from time zero of the saline- and SIA-treated rats was calculated and the final results were expressed after adjusting for the change in the control group. The effect of different doses of each peptide (4 to 80 µg) was determined. $ED_{50}$ values are presented as the dose of the protein resulting in one-half of the maximum hypoglycemic activity at 1 or 2 hr after SIA administration.

Construction of pSIA and pLPK-SIA

The SIA cDNA from pET-SIA was subcloned into the PCR-script sk+ (Invitrogen, San Diego, Calif.) at the BamHI/HindIII site. Then the SV40 poly(A) signal sequence from pCDM8 (Invitrogen) and the SV40 enhancer from the pGL3 (Promega, Madison, Wis.) were amplified by PCR and sub cloned at the HindIII/ApaI and ApaI sites, respectively. The albumin leader sequence (72 base pairs) was inserted in front of the SIA cDNA using a ExSite™ PCR-based Site-Directed Mutagenesis Kit (Stratagene, La Jolla, Calif.) using the following primer set: the 5' primer (63 mer) containing a sequence complementary to the upstream 27 nucleotides of the SIA cDNA and the 5' 36 nucleotides of the human albumin leader sequence (TTAGCTCGGC TTATTCCAGG GGTGTGTTTC GTCGAGATTT CGT-TAATCAG CACCTGTGCG GCT (SEQ ID NO:12)) and the 3' primer (63 mer) containing the 3' 36 nucleotides of the albumin leader sequence and the 27 nucleotides of the SIA cDNA (AGAGAAAAAG AAGGGAAATA AAGGT-TACCC ACTTCATGGA TCCGCCCAGT CGTCGACGCT GCT (SEQ ID NO:13)). The clone containing the albumin leader sequence was isolated and designated as pSIA. The final construct, pLPK-SIA, was generated by insertion of the promoter of the rat LPK gene (−3193 to +18) amplified by PCR into pSIA at the XbaI/SalI site.

Administration of pSIA, pLPK-SIA, rAAV-SIA or rAAV-LPK-SIA into the Liver

SD rats or NOD mice were anaesthetized with Ketamine-chloride (10 mg/kg) and ether. A midline abdominal incision was made, and 30 μg of DNA-FuGENE™ 6 (Boehringer Mannheim GmBH, Laval PQ) mixture, rAAV-SIA, or rAAV-LPK-SIA ($10^9$–$10^{12}$ virus particles) was injected into the hepatic portal veinof NOD mice or 11–13 week-old SD rats that had been in the hyperglycemic state for 2 weeks.

PCR and RT-PCR Analysis

To examine the presence of SIA DNA in plasmid-injected rats, PCR was performed using the sense primers derived from the T7 or LPK promoter region (5' GTAATACGACT-CACTATAG GGC 3' (SEQ ID NO:14) for pSIA-injected rats; 5' ATTTCGAATAAGAAGAGGAAGGGAAG 3' (SEQ ID NO:15) for pLPK-SIA-injected rats) and the antisense primers derived from the 3' terminus of the SIA gene (5' GCGCAAGCTTTTACTAGTTACAATAGTT 3' (SEQ ID NO:16). To detect SIA mRNA, the total RNA was isolated form various tissues and RT-PCR was performed using the primers 5' GCGCGGATCCATGTTCGTTAAT-CAGCAC 3' (SEQ ID NO:17) and 5' GCGCAAGCTTT-TACTAGTTACAATAGTT 3' (SEQ ID NO:18). β-actin mRNA was amplified as an internal control.

Production of Recombinant AAV-SIA and AAV-LPK-SIA

The 4.3 Kb LPK-SIA including the SV40 enhancer was amplified by PCR from the pLPK-SIA plasmid and subcloned into psub201 at the XbaI site. The resulting plasmid was designated as psub201-LPK-SIA. Human embryonic kidney 293 cells (ATCC CRL 1573, Manassas, Va.), grown in 15 cm dishes, were cotransfected with helper plasmid pXX2 and psub201-LPK-SIA using Lipofectamine plus reagent (Gibco-BRL) according to the manufacturer's protocol. The psub 201-SIA, which does not contain the LPK promoter, was used for the contruction of rAAV-SIA. After 6 h, the transfection medium was replaced with Iscove's modified Dulbecco's medium and the cells were infected with adenovirus type 5 dl312 at a multiplicity of infection (MOI) of 2. Three days after infection, the cells were harvested in HEPES buffer (140 mM NaCl, 25 mM HEPES, 0.7 mM $Na_2HPO_4$, pH 7.05) and lysed by three cycles of freezing and thawing. The cell lysate was centrifuged at 2,000×g for 20 min to remove cell debris. The recombinant virus (rAAV-SIA and rAAV-LPK-SIA) was purified through two rounds of cesium chloride equilibrium density gradients to remove any contaminating proteins. Purified rAAV-SIA or rAAV-LPK-SIA stock was heated at 56° C. for 45 min to inactivate residual adenoviral particles. For estimation of the number of rAAV-SIA or rAAV-LPK-SIA viral particles, each stock was treated with DNaseI and encapsulated viral DNA was extracted with phenol-chloroform and precipitated with ethanol. The amount of viral DNA was quantitated by competitive PCR (Muzyczka, N. Use of adeno-associated virus as a general transduction vector for mammalian cells. Curr. Top. Microbiol. Immunol. 158, 97–129 (1992)), incorporated herein by reference in its entirety.

Southern Blot Analysis

Total cellular DNA (10 μg) was isolated from the livers of normal control or rAAV-LPK-SIA-treated animals and digested with various restriction enzymes. After agarose gel electrophoresis, the DNA was transferred to a membrane and hybridized with a $^{32}$P-labeled probe containing the SIA cDNA and the SV40 sequence. The band was detected by autoradiography.

Measurement of Plasma Insulin, C-peptides, SIA and Blood Glucose

Plasma insulin and C-peptide levels were measured using the Linco rat insulin RIA kit and Linco rat C-peptide RA kit, respectively (Linco Research Immunoassy, St. Charles, Mo.). For the measurement of plasma SIA level, the inventors performed competitive ELISA using anti-SIA antibodies raised in rabbit, since SIA does not cross-react well with commercial anti-insulin antibodies. Blood glucose levels were measured or described elsewhere (Yoon, J. W., Lesniak, M. A., Fussganger R. & Notkins, A. L., "Genetic Differences In Suscepibitiliy Of Pancreatic β-Cells To Virus-Induced Diabetes Mellitus, Nature, 264, 178–180, (1976)).

Hyperglycemic clamp Experiment

STZ-induced diabetic rats were treated with $10^{11}$ particles of rAAV-LPK-SIA. At 30 weeks after the treatment, a 20% glucose solution, for maintenance of blood glucose at about 300 or 500 mg/dl, or saline, for maintenance of blood glucose at about 100 mg/dl, was perfused into the femoral vein using an electronic digital syringe pump (Harvard, South Natick, Mass.). After an equilibration period, blood glucose levels were determined immediately from the tail vein every 2 min, and the infusion rate was appropriately adjusted to maintain blood glucose levels at either approximately 100, 300, or 500 mg/dl for 30 min. The production of SIA in the hepatocytes and plasma was examined 4 hrs after glucose loading or saline treatment. Hyperglycemic clamp experiment is described in Cameron, N. E., Cotter, M. A. & Low, P. A., "Nerve Blood Flow In Early Experimental Diabetes In Rats: Relation To Conduction Deficits", AM. J. Physiol, 261, E1–E8, (1991).

Western Blot Analysis

The proteins below 30,000 m.w. were separated from 1.5 ml of respective pooled plasma at 0, 2, 4 and 6 h with centricon-30 (Amicon, Beverly, Mass.) and concentrated using a freeze-dryer. The concentrated proteins, with or without β-mercaptoethanol treatment, were electrophoretically separated on 10–20% tricine gradient gel (NOVEX, San Diego, Calif.) and transferred to nitrocellulose membrane. The SIA protein bands on blots were visualized with rabbit polyclonal anti-SIA antibody.

RNase Protection Assay

The [$^{32}$P]-labeled SIA antisense RNA was made from pET-SIA by in vitro transcription using T7 RNA polymerase. Ten μg of total RNA isolated from the livers of r-AAV-LPK-SIA-treated animals was hybridized with 8×$10^5$ cpm of labeled probes. After RNase treatment, the protected probes were resolved on a 6% denaturing polyacrylamide gel and autoradiography was performed.

Measurement of AST and ALT

AST and ALT were measured in an autochemical analyzer (Hitachi 747, Tokyo, Japan) using an ultraviolet assay method (Ma, Z., et al. Effect of hemoglobin- and Perflubron-based oxygen carriers on common clinical laboratory tests. Clin. Chem. 43, 1732–1737 (1997)).

Histological and Immunocytochemical Analysis

The liver and pancreas were removed, fixed in formalin and stained with hematoxylin and eosin to demonstrate general morphology (Yoon, J. W., Rodrigues, M. M., Currier, C. & Notkins, A. Long-term complications of virus-induced diabetes mellitus in mice. Nature 296, 566–569 (1982); and Yoon, J. W. et al. Control of autoimmune diabetes in NOD mice by GAD expression or suppression in cells. Science 284, 1183–1187 (1999)). Sections of liver and pancreas were also incubated with anti-SIA (made in rabbits) or anti-human insulin antibodies, respectively, and immunostained using a labeled streptavidin-biotin method (Dakopatts A/S, Glostrup, Denmark) and visualized by 3'-amino-9-ethylcarbazole (Dako, Santa Barbara, Calif., U.S.A) (Yoon, J. W. et al. Control of autoimmune diabetes in NOD mice by GAD expression or suppression in cells. i Science 284, 1183–1187 (1999); and Hirasawa K. et al. Possible role of macrophage-derived soluble mediators in the pathogenesis of EMC virus-induced diabetes in mice, J Virol. 71,4024–4031 (1997)).

Example 2

Results

The development of Type 1 diabetes, also known as insulin-dependent diabetes mellitus (IDDM), results from the almost total destruction of insulin-producing pancreatic β cells by β cell-specific autoimmune responses (Yoon, J. W. & Jun, H. S. Insulin-dependent diabetes mellitus. In: Roitt, I. M. & Delves, P. J. eds. Encyclopedia of Immunology, Second Edition. London, UK: Academic Press Ltd. pp. 1390–1398 (1998); Schranz, D. B. & Lernmark, A. Immunology in diabetes: an update. Diab. Metab. Rev. 14: 3–29 (1998); Tisch, R. & McDevitt, H. Insulin-dependent diabetes mellitus. Cell 85: 291–297 (1996); Bach, J. F. Insulin-dependent diabetes mellitus as a β cell targeted disease of immunoregulation. J. Autoimmunity 8: 439–463 (1995); and Rossini, A. A., Greiner, D. L., Friedman, H. P. & Mordes, J. P. Immunopathogenesis of diabetes mellitus. Diabetes Rev. 1: 43–75, (1993)). Standard insulin therapy may not maintain blood glucose concentrations within the relatively narrow range that occurs in normal pancreatic β cells (The Diabetes Control and Complications Trial Research Group. The effect of intensive treatment of diabetes on the development and progression of long-term complications in insulin-dependent diabetes mellitus. New Engl. J. Med. 329, 977–986 (1993)). The inventors have approached the permanent cure of IDDM by means of a novel gene therapy using a single-chain insulin analog, which possesses biologically active insulin activity without processing, and a glucose regulatable promoter, hepatocyte-specific L-type pyruvate kinase (LPK) promoter.

First, the inventors generated a single-chain insulin analog (SIA-1) by replacing 35 residues of the C-peptide with a short turn-forming heptapeptide (Gly-Gly-Gly-Pro-Gly-Lys-Arg). The inventors produced recombinant SIA-1 in Escherichia coli, refolded it, and examined its biological activity using receptor binding and glucose uptake assays. The inventors found that the receptor binding activity of SIA-1 was 12-fold higher than that of proinsulin and 3- to 4-fold lower than that of insulin. Similarly, the glucose uptake activity of SIA-1 was 16-fold higher than that of proinsulin and 4- to 5-fold lower than that of insulin. To determine whether SIA has a sufficient capability to control blood glucose in animals, as does insulin, the inventors administered SIA to 8 week-old Sprague-Dawley (SD) rats and determined the concentration of glucose in the whole blood. The inventors found that the hypoglycemic effect of SIA was 2- to 3-fold higher than that of proinsulin and 2-fold lower than that of insulin. This result indicates that the biological activity of the recombinant SIA is somewhat comparable to that of insulin.

Figure 1B:
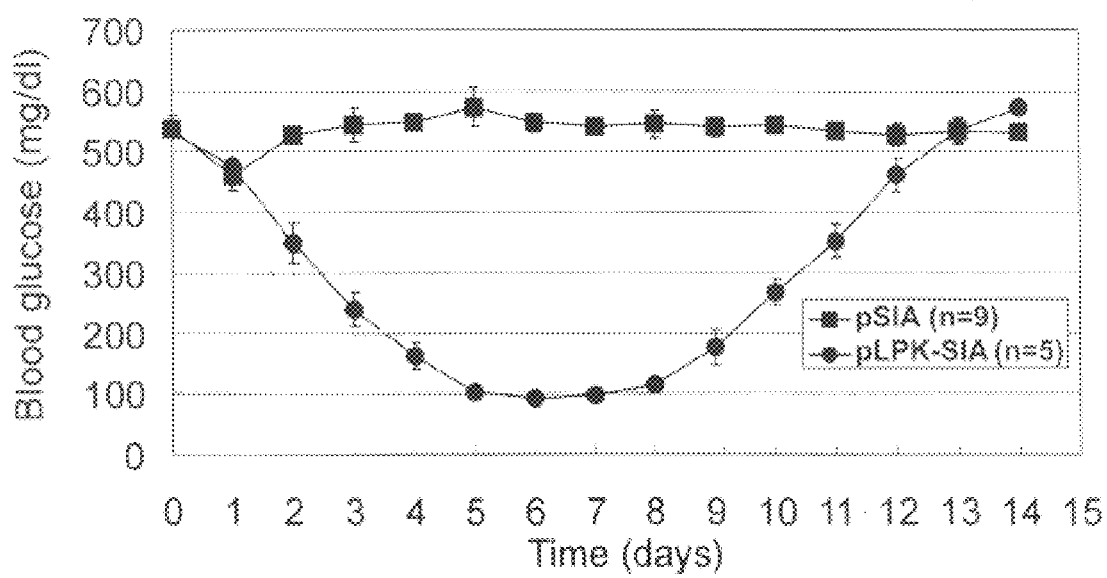
Figure 1C:
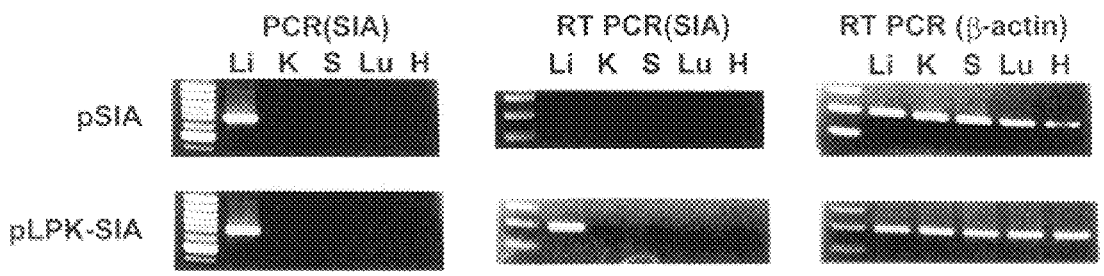

Second, the inventors constructed a recombinant plasmid, pLPK-SIA (FIG. 1A) by cloning the SIA gene under the LPK promoter (Cuif, M. H., Doiron, B. & Kahn, A. Insulin and cyclic AMP act at different levels on transcription of the L-type pyruvate kinase gene. FEBS Lett. 417, 81–84 (1997); Chen, R., Doiron, B. & Kahn, A. Glucose responsiveness of a reporter gene transduced into hepatocytic cells using a retroviral vector. FEBS Lett. 365, 223–226 (1995); Decaux, J. F., Antoine, B. & Kahn, A. Regulation of the expression of the L-type pyruvate kinase gene in adult rat hepatocytes in primary culture. J. Biol. Chem. 264, 11584–11590 (1989); Cuif, M. H., Porteu, A., Kahn, A. & Vaulont, S. Exploration of a liver-specific, glucose/insulin-responsive promoter in transgenic mice. J. Biol. Chem. 268, 13769–13772 (1993); and Bergot, M. O., Diaz-Guerra, M. J., Puzenat, N., Raymondjean, M. & Kahn, A. Cis-regulation of the L-type pyruvate kinase gene promoter by glucose, insulin and cyclic AMP. Nucleic Acids Res. 20, 1871–1877 (1992)), which will regulate SIA gene expression depending on the level of blood glucose. The albumin leader sequence (24 amino acids) was added to the frame of the SIA gene construct to facilitate the secretion of SIA from the hepatocytes. To determine whether pLPK-SIA can control IDDM by inducing the proper secretion of biologically active insulin analogue, the inventors mixed the pLPK-SIA with FuGENE™ 6 and administered it into the portal vein of streptozotocin (STZ)-induced diabetic SD rats. The inventors found that the blood glucose levels gradually decreased in the pLPK-SIA-injected rats until the fifth day after the administration and remained in a normoglycemic state for an additional 4 days. However, the blood glucose levels of the pLPK-SIA-injected rats gradually increased to reach 500 mg/dl at 14 days after treatment (FIG. 1B). In contrast, the blood glucose levels were not changed in the STZ-induced diabetic rats that were administered with the SIA construct without pLPK (FIG. 1B). To determine whether the plasmid DNA was specifically transfected into the liver and whether the SIA mRNAs were selectively expressed in the liver cells, the inventors examined the presence of the injected DNA and the expression of SIA mRNA in various organs including the liver, kidney, spleen, lung and heart from both groups of the rats at 5 days after the plasmid administration. The inventors found that the transfected plasmid DNAs were detected in only liver cells from both groups of rats, whereas SIA mRNA was expressed in only the pLPK-SIA-treated rats (FIG. 1C). Through these studies, the inventors found that SIA mRNA was exclusively expressed in the liver of the pLPK-SIA-treated rats, the treatment of diabetic rats with pLPK-SIA resulted in the transient remission of IDDM, and hyperglycemia recurred within 14 days after treatment probably due to the short half-life of the transfected pLPK-SIA DNA in the rat.

Third, the inventors attempted to overcome the short half-life of transfected DNA using adeno-associated virus (AAV) vector, since it has been shown to be a safe and efficient gene delivery system (Muzyczka, N. Use of adeno-associated virus as a general transduction vector for mammalian cells. *Curr. Top. Microbiol. Immunol.* 158, 97–129 (1992); and Clark, K. R., Liu, X., McGrath, J. P. & Johnson, P. R. Highly purified recombinant adeno-associated virus vectors are biologically active and free of detectable helper and wild-type viruses. *Human Gene Therapy* 10, 1031–1039 (1999)), and integrates into the host chromosomal DNA in a site-specific manner (Samulski, R. J. Adeno-associated virus: integration at a specific chromosomal locus. *Curr. Opin. Genet. Dev.* 3, 74–80 (1993); Giraud, C., Winocour, E. & Berns, K. I. Site-specific integration by adeno-associated virus is directed by a cellular DNA sequence. *Proc. Natl. Acad. Sci. USA* 91, 10039–10043 (1994); and Kotin, R. M., Linden, R.

Figure 2A:
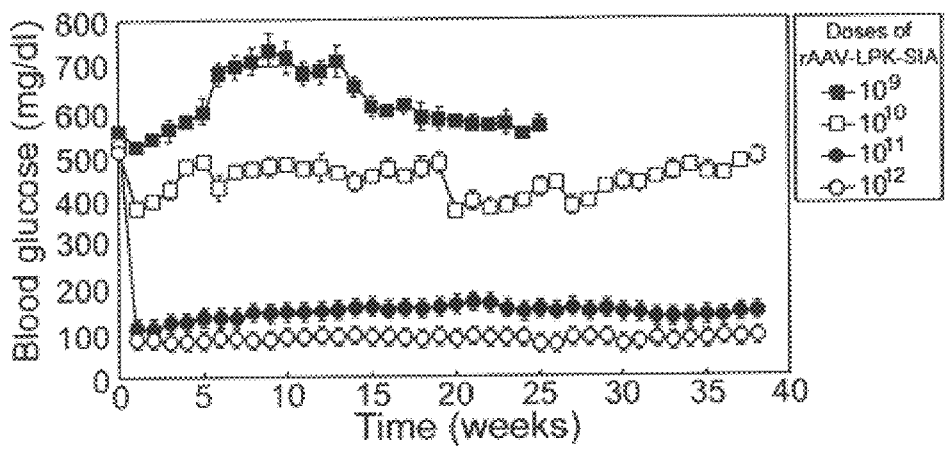

M. & Berns, K. I. Characterization of a preferred site on human chromosome 19 q for integration of adeno-associated virus DNA by non-homologous recombination. *EMBO J.* 11, 5071–5078 (1992)). The inventors produced recombinant AAV containing LPK promoter-SIA DNA (rAAV-LPK-SIA) in 293 cells. To determine whether rAAV-LPK-SIA can efficiently and permanently control IDDM, the inventors administered rAAV-LPK-SIA through the portal vein of STZ-induced diabetic SD rats. The blood glucose levels gradually decreased in the rAAV-LPK-SIA-treated rats ($10^{11}$ virus particles/rat), reached the level of normoglycemia one-week after treatment, and remained in a normoglycemic state for more than 8 months without hypoglycemic or any apparent side effects (FIG. 2A). However, lower doses of rAAV-LPK-SIA ($10^9$–$10^{10}$ virus particles) appeared to be insufficient for complete remission. To determine whether the treatment of diabetic rats with a dose higher than the curable optimum dose ($10^{11}$ virus particles of rAAV-LPK-SIA) might result in hypoglycemia, the inventors administered a 10-fold higher dose of rAAV-LPK-SIA ($10^{12}$ virus particles of rAAV-LPK-SIA). None of the treated animals became hypoglycemic, indicating that the expression of SIA under the LPK promoter is properly regulated by the level of blood glucose. The body weight of the animals treated with $10^{11}$ virus particles of rAAV-LPK-SIA showed body weight similar to normal rats.

Figure 2B:
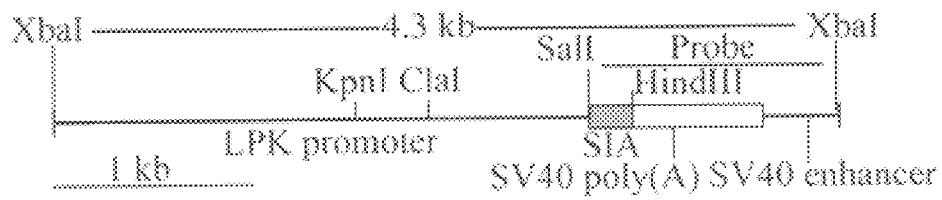
Figure 2B:
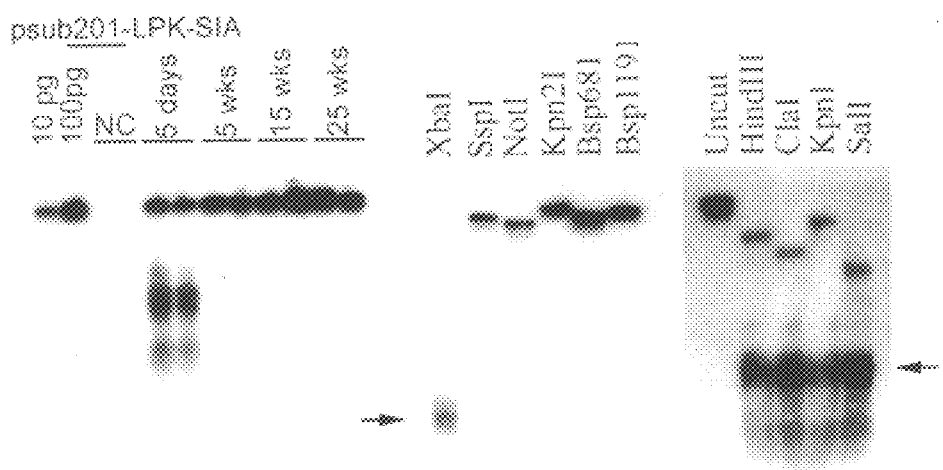

The inventors then attempted to find the molecular state of the AAV genome in the recipients of rAAV-LPK-SIA. The inventors removed livers from rats treated with the curable optimum dose of rAAV-LPK-SIA at 5 days, 5 weeks, 15 weeks and 25 weeks after treatment, extracted the DNA and performed southern blot with SIA cDNA and the SV40 sequence as a probe. The inventors found that rAAV DNA exists in both single-stranded and double-stranded states at the early stage (5 days) after the treatment, but found only the double-stranded state at a later stage (5–25 weeks) after the treatment. When the inventors examined the integration of rAAV-LPK-SIA DNA in the hepatocyte DNA at 25 weeks after the treatment, rAAV-LPK-SIA DNA was found to be integrated into the chromosomal DNA in a head-to-tail concatemeric manner (FIG. 2B). These results indicate that the single-stranded recombinant adeno-associated viral genome is converted to a double-stranded genome in the infected hepatocytes.

Figure 2C:
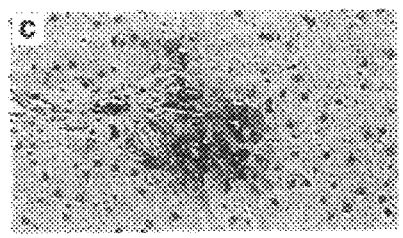
Figure 2D:
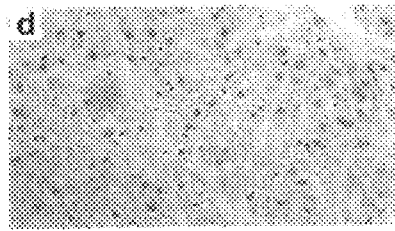
Figure 2E:
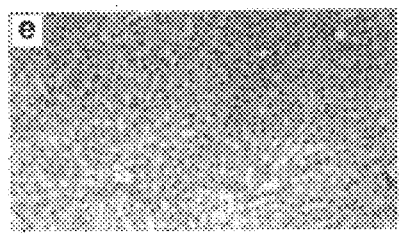
Figure 2F:
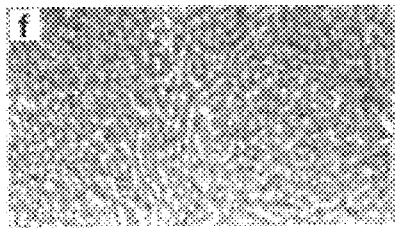
Figure 2G:
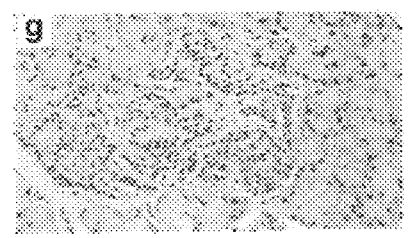

The inventors also determined the localization of SIA-expression in the liver of rats treated with rAAV-LPK-SIA by immunohistochemical staining of liver sections with anti-SIA antibody. The inventors found that SIA is expressed in the hepatocytes of the liver from the rAAV-LPK-SIA-treated rats (FIG. 2C), but not in the liver from untreated control rats (FIG. 2D). SIA-expressing cells were clustered around the central vein and portal triads in the liver (FIG. 2C). To determine whether infection of hepatocytes with rAAV-LPK-SIA results in damage to the infected cells, the inventors histologically examined the infected liver sections. The inventors found that there was no difference between untreated rats and rAAV-LPK-SIA-treated rats (FIGS. 2E and 2F). The inventors then determined whether prolonged hepatic SIA expression causes any other liver damage by liver function tests. The inventors found no difference in the level of plasma aspartate transaminase (AST) or plasma alanine transaminase (ALT), marker enzymes for hepatic damage, between saline-treated control rats (94±12 IU/l for AST and 46±9 IU/l for ALT; n=5) and rAAV-LPK-SIA-treated rats (95±10 IU/l for AST and 40±9 IU/l for ALT), indicating that rAAV-LPK-SIA treatment does not cause liver damage. The inventors also examined the development of antibodies against SIA every five weeks until 8 months after treatment and found that anti-SIA antibody was barely detected in the sera of the treated rats (data not shown). These results indicate that treatment of diabetic rats with rAAV-LPK-SIA resulted in the remission of diabetes without any apparent change in the infected liver cells or any adverse effects of SIA expression on the hepatocytes.

Figure 2H:
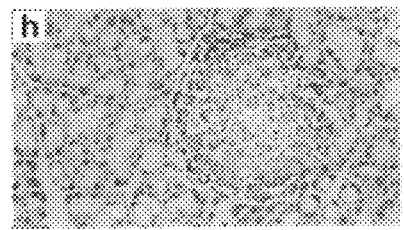
Figure 2I:
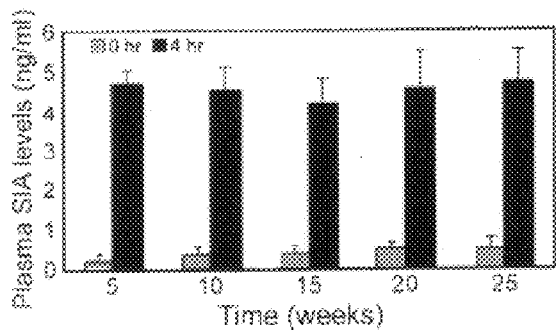
Figure 2J:
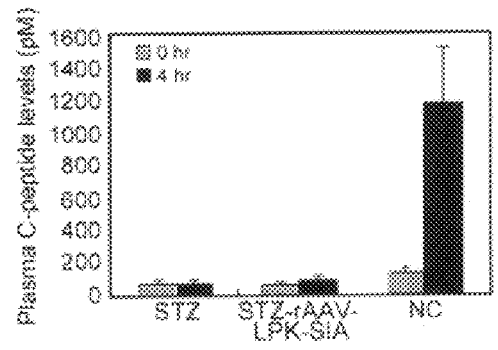

Then, the inventors questioned whether the remission of diabetes might be due to the secretion of insulin from the residual pancreatic β cells in the STZ-treated rats, rather than the expression of SIA. The inventors stained pancreatic sections from rAAV-LPK-SIA-treated rats with anti-insulin antibody, and found that insulin-producing β cells were rarely found in these islets (FIG. 2G) whereas abundant insulin-producing β cells were found in the islets of untreated normal rats (FIG. 2H). When SIA levels in the plasma of the rats were examined every 5 weeks after treatment, it was found that SIA was continuously produced for over 8 months after the treatment with rAAV-LPK-SIA (FIG. 2I; data after 25 weeks not shown). In addition, the C-peptide level in the rAAV-LPK-SIA-treated rats after glucose loading was measured. A negligible amount of C-peptide was found in plasma of the rats, whereas a substantial amount of C-peptide was found in plasma of nondiabetic normal rats (FIG. 2J). These results indicate that the control of blood glucose in rAAV-LPK-SIA-treated rats was not due to endogenous pancreatic insulin, but to the expression of SIA in the liver cells.

Fourth, the inventors questioned whether the expression of SIA is truly regulated by blood glucose levels through the LPK promoter. A 20% glucose solution or saline was perfused into the femoral vein using an electronic digital syringe pump (Cameron, N. E., Cotter, M. A. & Low, P. A., "Nerve Blood Flow In Early Experimental Diabetes In Rats: Relation To Conduction Deficits", *AM J. Physiol,* 261, E1–E8, (1991)), and maintained different levels of blood glucose (approximately 100, 300, or 500 mg/dl) for 30 min in rats in which the blood glucose had been normalized after treatment with $10^{11}$ particles of rAAV-LPK-SIA, and examined the production of SIA in the hepatocytes and plasma at 4 hrs after glucose loading. The inventors found that the level of SIA expression was closely correlated with the concentration of blood glucose (FIGS. 3B and 3C), even though similar levels of SIA DNA were found among the different groups of rats (FIG. 3A), indicating that the expression of SIA under the LPK promoter is properly controlled by blood glucose levels.

Figure 3A:
Figure 3B:
Figure 3C:
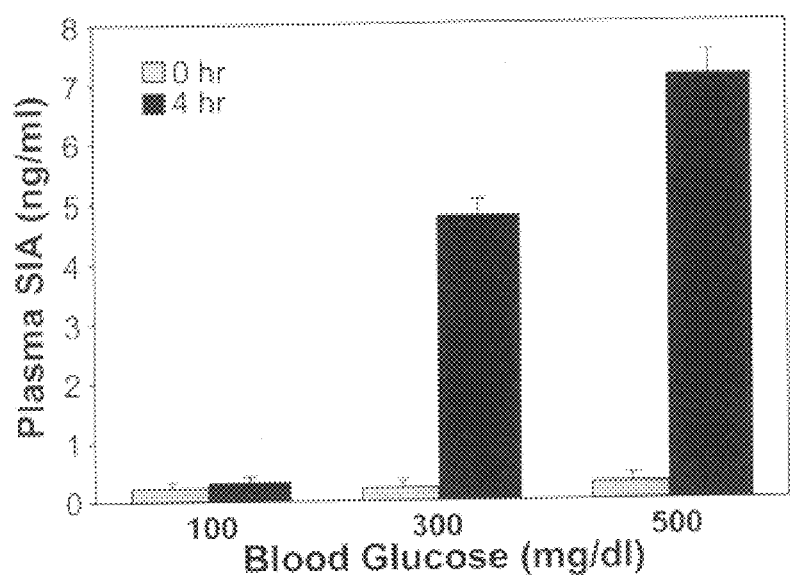
Figure 3D:
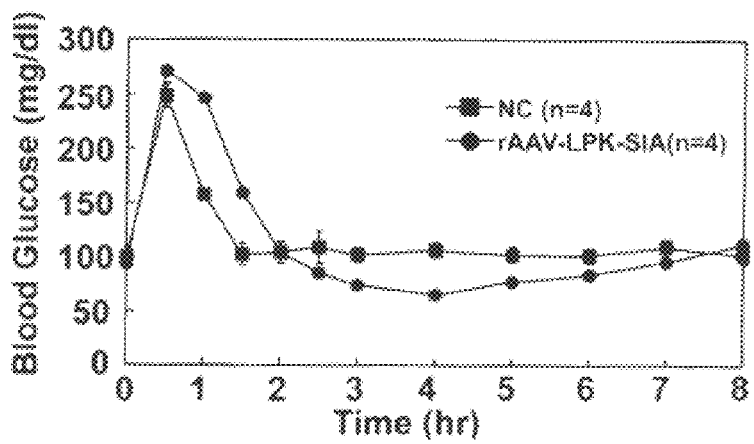
Figure 3E:
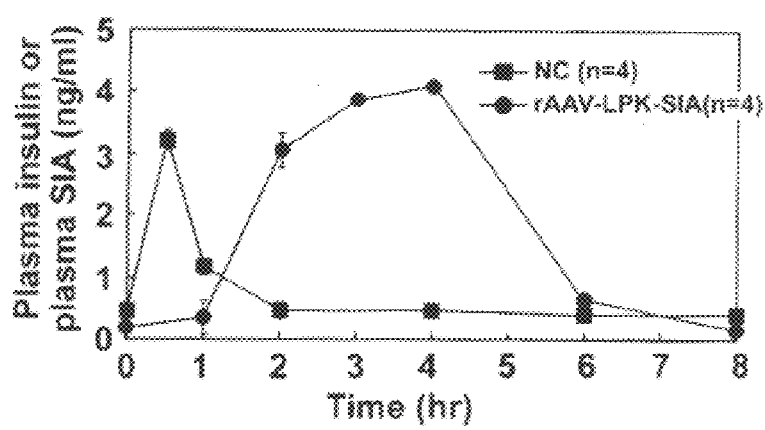
Figure 3F:
Figure 3G:

Next, the inventors determined whether rAAV-LPK-SIA-treated rats (15–17 weeks old) clear glucose from the blood in a manner similar to nondiabetic normal rats by glucose tolerance tests (GTT). The inventors injected glucose (2 g/kg body weight i.p.) into rAAV-LPK-SIA-treated rats, which had recovered from diabetes, after four hours of fasting and examined the blood glucose, plasma insulin and glucagon levels at different times after glucose loading. The inventors found that the blood glucose levels of normal rats peaked at 30 min after glucose loading, returned to the normal range (around 100 mg/dl) at 90 min, and stabilized thereafter (FIG. 3D). The blood glucose levels of rAAV-LPK-SIA-treated rats showed a similar pattern as compared to normal rats, except for a slightly delayed recovery time to reach normal glucose levels (120 min vs. 90 min) and transient by lower blood glucose levels from 3 to 6 hrs after glucose loading 3D). The plasma insulin levels of normal rats rapidly peaked within 30 min and returned to basal levels at 2 hrs after glucose loading (FIG. 3E). However, the plasma SIA levels of rAAV-LPK-SIA-treated rats peaked at 3–4 hrs and returned to basal levels at 6 hrs after glucose loading (FIGS. 3E and 3F). The expression of SIA mRNA in the hepatocytes showed a similar pattern to that of plasma SIA (FIG. 3G). The response of insulin to glucose in normal rats was very rapid, since insulin is released in normal pancreatic β cells through the process of exocytosis. Although the blood glucose levels of normal and rAAV-LPK-SIA-treated rats were relatively similar, the plasma SIA levels from 2 to 5 hours after the glucose loading were significantly higher than the plasma insulin levels of normal rats. This is probably due to the delayed metabolic processing of SIA, resulting in its longer half-life in the circulation. The slightly lower blood glucose levels in rAAV-LPK-SIA-treated rats from 3 to 6 hr after glucose loading may be due to this prolonged half-life of SIA. As a matter of fact, the secretion of SIA in rAAV-LPK-SIA-treated rats is controlled at the transcriptional level, and thus a prolonged period of time is required to change the plasma SIA levels in response to blood glucose levels, resulting in the prolonged secretion of SIA during GTT in rAAV-LPK-SIA-treated rats. In contrast, insulin is released in normal pancreatic β cells through the process of exocytosis so the insulin response to glucose was rapid in normal cells. The major physical determinant of insulin secretion in the β cells is the concentration of blood glucose. β cells are very sensitive to small changes in extracellular glucose within a narrow physiological range. Thus, the plasma insulin level in normal rats is concomitantly increased with the blood glucose level during GTT. However, the plasma SIA levels in rAAV-LPK-SIA-treated rats are not tightly correlated with the blood glucose levels after glucose loading. Nevertheless, the non-fasting blood glucose levels of rAAV-LPK-SIA-treated rats were always within the normoglycemic range, implying that the expression of SIA is efficiently regulated by the level of glucose. In addition, the inventors measured the level of plasma glucagon in rAAV-LPK-SIA-treated rats, and found that it increased significantly at 6 hours after glucose loading. The increase in glucagon levels correlates with the decrease in plasma levels of SIA and its mRNA (FIGS. 3B, 3C and 3E), suggesting that functional α-cells in the pancreatic islets are required for negative feedback regulation on the LPK promoter-mediated SIA expression in rAAV-LPK-SIA-treated rats.

Figure 4A:
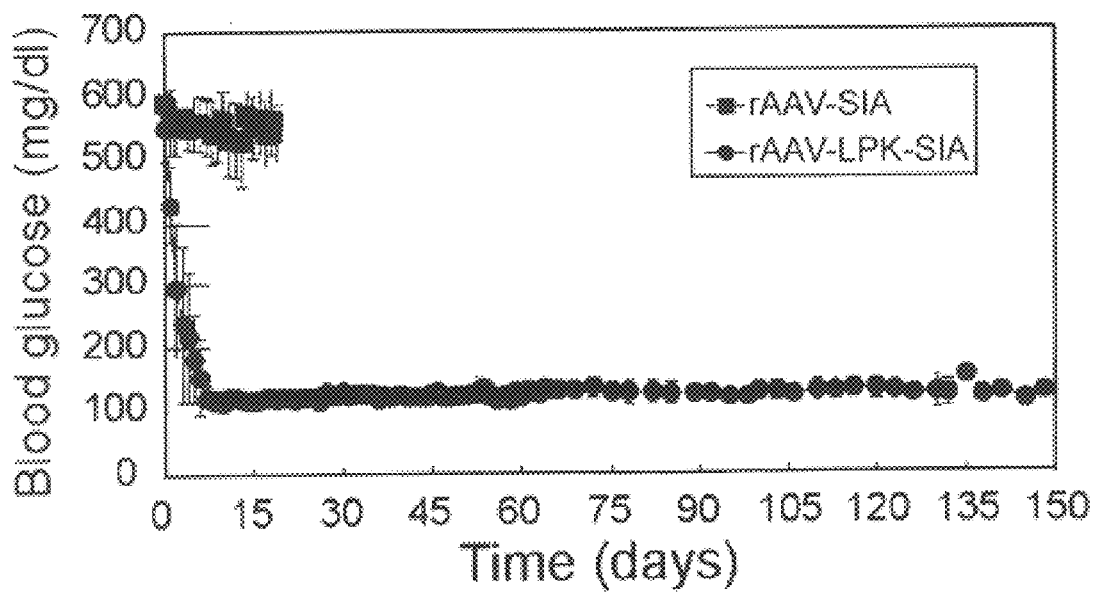
Figure 4B:
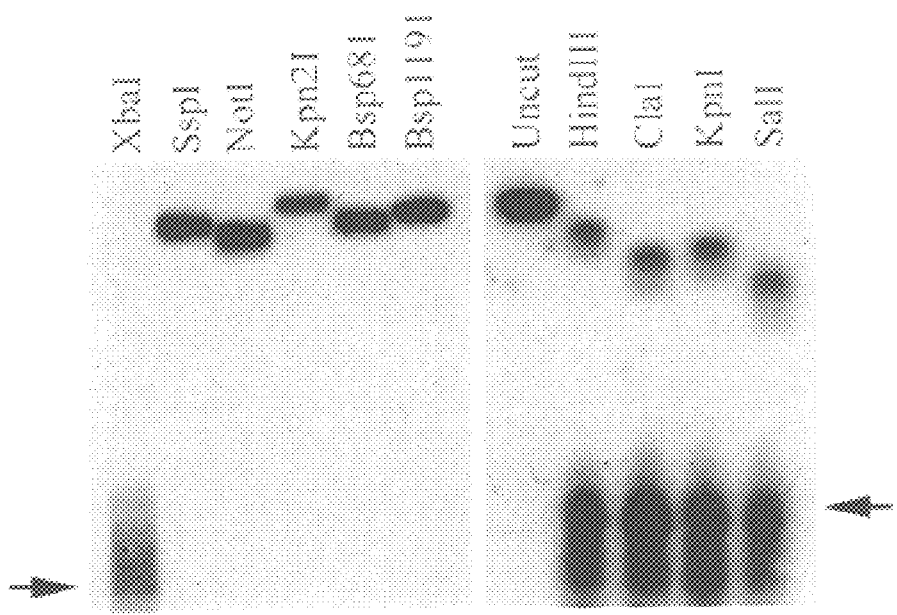
Figure 4C:
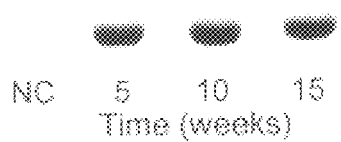
Figure 4D:
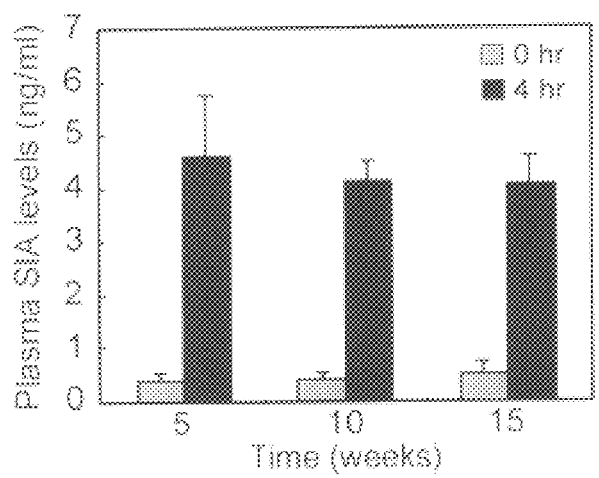

Fifth, the inventors attempted to find whether rAAV-LPK-SIA can also permanently control autoimmune diabetes in non-obese diabetic (NOD) mice as in STZ-induced diabetes in rats. The inventors administered rAAV-LPK-SIA into diabetic NOD mice by intraportal injection and monitored the blood glucose levels. The blood glucose levels gradually decreased in the rAAV-LPK-SIA-treated NOD mice ($10^{12}$ virus particles), reached the level of normoglycemia at 7 days after treatment, and remained in a normoglycemic state for more than 5 months. In contrast, diabetic NOD mice treated with rAAV-SIA (without the LPK promoter) remained hyperglycemic and died within 3 weeks (FIG. 4A). When the presence of the SIA gene in the hepatocytes of NOD mice were examined at 15 weeks after treatment with rAAV-LPK-SIA, it was discovered that SIA DNA was integrated into the chromosomal DNA (FIG. 4B). SIA expression was then examined in the liver and plasma of the mice after glucose loading at 5, 10, and 15 weeks after treatment with rAAV-LPK-SIA, and found that SIA mRNA was clearly expressed and SIA protein was released in the plasma (FIGS. 4C and 4D). Anti-SIA antibody was not detected in the sera from these mice during the 5 months after treatment (data not shown).

Figure 4E:
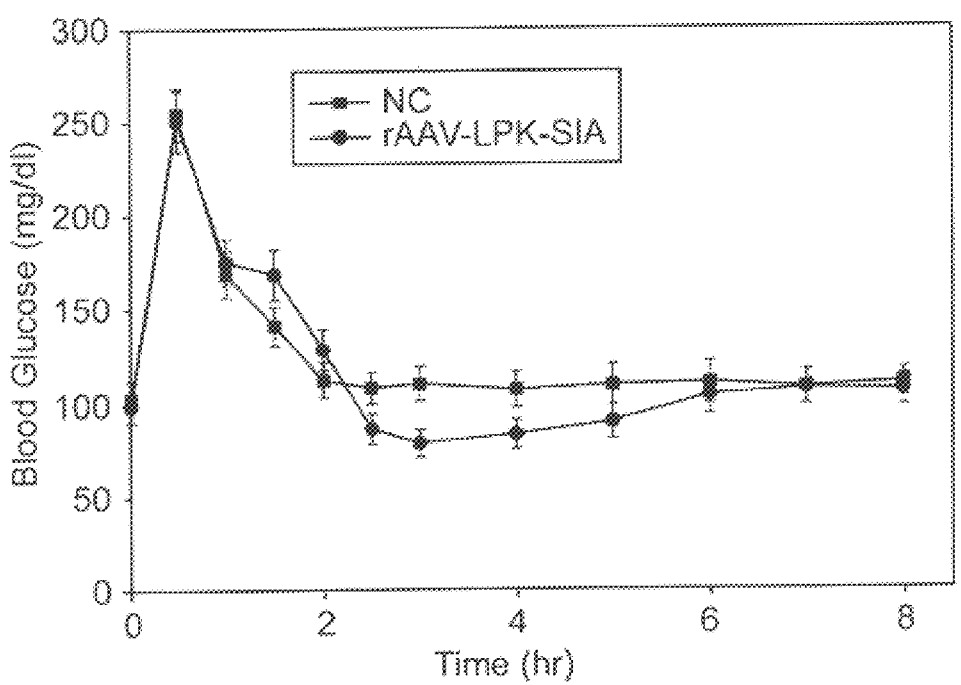

In addition, the inventors performed GTT in NOD mice which had recovered from diabetes. The inventors found that the blood glucose levels of rAAV-SIA-treated NOD mice peaked at 30 min after glucose loading, returned to the normal range (115 mg/dl at 120 min) and stabilized thereafter (FIG. 4E). The time of the peak blood glucose levels in these mice was similar to that found in normal ICR mice, but there was a delay in the recovery time to reach normal blood glucose levels and slightly lower blood glucose levels from 3 to 6 hours after glucose loading as compared with normal controls, as seen in the rAAV-SIA-treated rats.

The inventors have developed a potential method for the treatment of autoimmune type 1 diabetes by the expression of a single-chain insulin analog in the hepatocytes under the control of hepatocyte-specific glucose regulatable promoter and optionally an SV40 enhancer. The host's cell-mediated autoimmune responses do not attack the SIA-expressing hepatocytes, resulting in the permanent remission of autoimmune diabetes in NOD mice. The treatment of both chemically induced diabetes in rats and autoimmune diabetes in NOD mice with rAAV expressing the insulin analog resulted in the permanent remission of type 1 diabetes without any detectable adverse effect on the hepatocytes, suggesting that this novel gene therapy may have therapeutic value for the cure of type 1 diabetes in humans.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

REFERENCES

1. Levine, F. & Leibowitz, G. Towards gene therapy of diabetes mellitus. *Mol. Med. Today* 5, 165–171 (1999).
2. Yoon, J. W. & Jun, H. S. Insulin-dependent diabetes mellitus. In: Roitt, I. M. & Delves, P. J. eds. *Encyclopedia of Immunology, Second Edition.* London, UK: Academic Press Ltd. pp. 1390–1398 (1998).
3. Schranz, D. B. & Lernmark, A. Immunology in diabetes: an update. *Diab. Metab. Rev.* 14: 3–29 (1998).
4. Tisch, R. & McDevitt, H. Insulin-dependent diabetes mellitus. *Cell* 85: 291–297 (1996).
5. Bach, J. F. Insulin-dependent diabetes mellitus as a β cell targeted disease of immunoregulation. *J. Autoimmunity* 8: 439–463 (1995).
6. Rossini, A. A., Greiner, D. L., Friedman, H. P. & Mordes, J. P. Immunopathogenesis of diabetes mellitus. *Diabetes Rev.* 1: 43–75, (1993).

7. The Diabetes Control and Complications Trial Research Group. The effect of intensive treatment of diabetes on the development and progression of long-term complications in insulin-dependent diabetes mellitus. *New Engl. J. Med.* 329, 977–986 (1993).
8. Cuif, M. H., Doiron, B. & Kahn, A. Insulin and cyclic AMP act at different levels on transcription of the L-type pyruvate kinase gene. *FEBS Lett.* 417, 81–84 (1997).
9. Chen, R., Doiron, B. & Kahn, A. Glucose responsiveness of a reporter gene transduced into hepatocytic cells using a retroviral vector. *FEBS Lett.* 365, 223–226 (1995).
10. Decaux, J. F., Antoine, B. & Kahn, A. Regulation of the expression of the L-type pyruvate kinase gene in adult rat hepatocytes in primary culture. *J. Biol. Chem.* 264, 11584–11590 (1989).
11. Cuif, M. H., Porteu, A., Kahn, A. & Vaulont, S. Exploration of a liver-specific, glucose/insulin-responsive promoter in transgenic mice. *J. Biol. Chem.* 268, 13769–13772 (1993).
12. Bergot, M. O., Diaz-Guerra, M. J., Puzenat, N., Raymondjean, M. & Kahn, A. Cis-regulation of the L-type pyruvate kinase gene promoter by glucose, insulin and cyclic AMP. *Nucleic Acids Res.* 20, 1871–1877 (1992).
13. Muzyczka, N. Use of adeno-associated virus as a general transduction vector for mammalian cells. *Curr. Top. Microbiol. Immunol.* 158, 97–129 (1992).
14. Clark, K. R., Liu, X., McGrath, J. P. & Johnson, P. R. Highly purified recombinant adeno-associated virus vectors are biologically active and free of detectable helper and wild-type viruses. *Human Gene Therapy* 10, 1031–1039 (1999).
15. Samulski, R. J. Adeno-associated virus: integration at a specific chromosomal locus. *Curr. Opin. Genet. Dev.* 3, 74–80 (1993).
16. Giraud, C., Winocour, E. & Berns, K. I. Site-specific integration by adeno-associated virus is directed by a cellular DNA sequence. *Proc. Natl. Acad. Sci. USA* 91, 10039–10043 (1994).
17. Kotin, R. M., Linden, R. M. & Berns, K. I. Characterization of a preferred site on human chromosome 19q for integration of adeno-associated virus DNA by non-homologous recombination. *EMBO J.* 11, 5071–5078 (1992).
18. Studier, F. W., Rosenberg, A. H., Dunn, J. J. & Dubendorff, J. W. Use of T7 RNA polymerase to direct expression of cloned genes. *Methods Enzymol.* 185, 60–89 (1990).
19. Pollet, R. J., Standaert, M. L. & Haase, B. A. Insulin binding to the human lymphocyte receptor. Evaluation of the negative cooperativity model. *J. Biol. Chem.* 252, 5828–5834 (1977).
20. Roth, J. Assay of peptide hormones using cell receptors: application to insulin and to human growth hormone. *Methods Enzymol.* 37, 66–82 (1975).
21. Frost, S. C. & Lane, M. D. Evidence for the involvement of vicinal sulfhydryl groups in insulin-activated hexose transport by 3T3-L I adipocytes. *J. Biol. Chem.* 260, 2646–2652 (1985).
22. Heath, W. F., et al. (A-C-B) human proinsulin, a novel insulin agonist and intermediate in the synthesis of biosynthetic human insulin. *J. Biol. Chem.* 267, 419–425 (1992).
23. Ma, Z., et al. Effect of hemoglobin- and Perflubron-based oxygen carriers on common clinical laboratory tests. *Clin. Chem.* 43, 1732–1737 (1997).
24. Yoon, J. W., Rodrigues, M. M., Currier, C. & Notkins, A. Long-term complications of virus-induced diabetes mellitus in mice. *Nature* 296, 566–569 (1982).
25. Yoon, J. W. et al. Control of autoimmune diabetes in NOD mice by GAD expression or suppression in cells. *Science* 284, 1183–1187 (1999).
26. Hirasawa K. et al. Possible role of macrophage-derived soluble mediators in the pathogenesis of EMC virus-induced diabetes in mice, *J Virol.* 71,4024–4031 (1997).
27. Cameron, N. E., Cotter, M. A. & Low, P. A., Nerve blood flow in early experimental diabetes in rats: realtion to conduction deficits, *Am J. Physiol.* 261, E1–E8 (1991).
28. Yoon, J. W., Lesniak, M. A., Fussganger, R. & Notkins, A. L., Genetic differences in susceptibitiy of pancreatic β-cells to virus-induced diabetews mellitus., *Nature* 264, 178–180, (1976).

What is claimed is:

1. A single-chain insulin analog compound of formula (I) having the properties of greater insulin receptor binding activity than proinsulin and less insulin receptor binding activity than insulin:

$$\text{B chain-X-A chain} \qquad (I)$$

wherein:

B and A chains are the human insulin chains, respectively; and

X is a joining peptide of about 5 to 18 amino acids comprising the following sequence:
Gly-Gly-Gly-Pro-Gly-Lys-Arg (SEQ ID NO: 1).

2. A polynucleotide comprising the nucleic acid sequence of SEQ ID NO:3 that encodes the single-chain insulin analog according to claim 1.

3. A recombinant vector comprising the polynucleotide according to claim 2.

4. The vector according to claim 3, wherein said vector is a plasmid.

5. The vector according to claim 3, wherein said vector is a virus.

6. The vector according to claim 5, wherein said virus is adeno-associated virus.

7. The vector according to claim 3, comprising an inducible promoter.

8. The vector according to claim 7, wherein said promoter is regulated by glucose.

9. The vector according to claim 8, wherein said promoter is a pyruvate kinase gene promoter.

10. The vector according to claim 9, wherein said promoter is a hepatocyte-specific L-type pyruvate kinase gene promoter.

11. A cell line transformed with the vector according to claim 3.

* * * * *

UNITED STATES PATENT AND TRADEMARK OFFICE
CERTIFICATE OF CORRECTION

PATENT NO. : 6,630,348 B1
DATED : October 7, 2003
INVENTOR(S) : Lee et al.

It is certified that error appears in the above-identified patent and that said Letters Patent is hereby corrected as shown below:

<u>Title page,</u>
Insert Item -- [73] Assignee: Yonsei University, Seoul, Korea --

Signed and Sealed this

Thirtieth Day of November, 2004

JON W. DUDAS
*Director of the United States Patent and Trademark Office*